United States Patent
Lynch et al.

(10) Patent No.: US 12,403,094 B2
(45) Date of Patent: *Sep. 2, 2025

(54) RHEOLOGICAL SOLID ORAL COMPOSITION

(71) Applicant: The Procter & Gamble Company, Cincinnati, OH (US)

(72) Inventors: Matthew Lawrence Lynch, Mariemont, OH (US); Scott Kendyl Stanley, Mason, OH (US); Brandon Philip Illie, Felicity, OH (US); Taotao Zhu, West Chester, OH (US); Jamie Lynn Dria, Deerfield Township, OH (US); Ashraf Traboulsi, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/225,149

(22) Filed: Apr. 8, 2021

(65) Prior Publication Data

US 2021/0322322 A1    Oct. 21, 2021

Related U.S. Application Data

(60) Provisional application No. 63/007,969, filed on Apr. 10, 2020.

(51) Int. Cl.
| | | |
|---|---|---|
| *A61K 9/20* | (2006.01) |
| *A61K 9/28* | (2006.01) |
| *A61K 31/137* | (2006.01) |
| *A61K 31/138* | (2006.01) |
| *A61K 31/167* | (2006.01) |
| *A61K 31/4402* | (2006.01) |
| *A61K 47/12* | (2006.01) |

(52) U.S. Cl.
CPC ............ *A61K 9/2013* (2013.01); *A61K 9/282* (2013.01); *A61K 31/137* (2013.01); *A61K 31/138* (2013.01); *A61K 31/167* (2013.01); *A61K 31/4402* (2013.01); *A61K 47/12* (2013.01)

(58) Field of Classification Search
None
See application file for complete search history.

(56) References Cited

U.S. PATENT DOCUMENTS

| | | |
|---|---|---|
| 823,725 A | 6/1906 | Hayden |
| 3,112,219 A | 11/1963 | Alfred |
| 3,293,684 A | 12/1966 | Otto |
| 3,585,144 A | 6/1971 | Schiltz |
| 3,810,841 A | 5/1974 | Richter |
| 3,956,158 A | 5/1976 | Donaldson |
| 4,107,289 A | 8/1978 | Kaufman |
| 4,203,857 A | 5/1980 | Dugan |
| 4,226,889 A * | 10/1980 | Yuhas ............... A61K 8/042 424/59 |
| 4,322,400 A | 3/1982 | Yuhas |
| 4,486,404 A | 12/1984 | Weinert |
| 4,806,340 A | 2/1989 | Gaffar |
| 4,808,467 A | 2/1989 | Suskind et al. |
| 5,144,729 A | 9/1992 | Austin et al. |
| 5,160,739 A | 11/1992 | Kanga |
| 5,340,492 A * | 8/1994 | Kacher ............... C11D 17/006 510/491 |
| 5,340,571 A | 8/1994 | Grace |
| 5,425,892 A | 6/1995 | Taneri et al. |
| 5,436,278 A | 7/1995 | Imashiro et al. |
| 5,525,397 A | 6/1996 | Shizuno et al. |
| 5,585,092 A | 12/1996 | Trandai et al. |
| 5,605,681 A * | 2/1997 | Trandai ............... A61K 8/361 424/65 |
| 5,691,035 A | 11/1997 | Chappell et al. |
| 5,846,520 A | 12/1998 | Guskey et al. |
| 5,916,590 A * | 6/1999 | Cody ............... A61P 25/04 424/455 |
| 6,042,815 A | 3/2000 | Kellner et al. |
| 6,143,393 A | 11/2000 | Abe et al. |
| 6,241,835 B1 | 6/2001 | Abe et al. |
| 6,245,413 B1 | 6/2001 | Kenmochi et al. |
| 6,329,308 B1 | 12/2001 | Kenmochi et al. |
| 6,550,092 B1 | 4/2003 | Brown et al. |
| 6,554,937 B1 | 4/2003 | Kenmochi et al. |
| 6,774,070 B1 | 8/2004 | Kenmochi et al. |
| 6,777,064 B1 | 8/2004 | Brown et al. |
| 6,797,357 B2 | 9/2004 | Fereshtehkhou et al. |
| 6,813,801 B2 | 11/2004 | Tanaka et al. |
| 6,936,330 B2 | 8/2005 | Fereshtehkhou et al. |
| 7,003,856 B2 | 2/2006 | Hayashi et al. |

(Continued)

FOREIGN PATENT DOCUMENTS

| | | |
|---|---|---|
| CA | 680113 A | 2/1964 |
| CN | 107440935 A | 12/2017 |

(Continued)

OTHER PUBLICATIONS

Saper, Am Fam Physician, 79, 9, 2009 (Year: 2009).*

(Continued)

*Primary Examiner* — Susan T Tran
*Assistant Examiner* — William Craigo
(74) *Attorney, Agent, or Firm* — Kathleen Y. Carter; James E. Oehlenschlager

(57) ABSTRACT

A rheological solid oral composition comprising a crystallizing agent, an aqueous phase, and an oral active agent.

15 Claims, 4 Drawing Sheets

(56) References Cited

U.S. PATENT DOCUMENTS

| | | |
|---|---|---|
| 7,041,277 B2 | 5/2006 | Holme |
| 7,291,359 B2 | 11/2007 | Haskett et al. |
| 7,386,907 B2 | 6/2008 | Otsuka et al. |
| 7,560,398 B2 | 7/2009 | Zillig et al. |
| 7,566,671 B2 | 7/2009 | Hoadley et al. |
| 7,712,178 B2 | 5/2010 | Yamada |
| 7,779,502 B2 | 8/2010 | Fujiwara et al. |
| 7,937,797 B2 | 5/2011 | Tsuchiya et al. |
| 8,075,977 B2 | 12/2011 | Curro et al. |
| 8,093,192 B2 | 1/2012 | Liu et al. |
| 8,146,197 B2 | 4/2012 | Yamada |
| 8,151,402 B2 | 4/2012 | Takabayashi et al. |
| 8,161,594 B2 | 4/2012 | Policicchio et al. |
| 8,186,001 B2 | 5/2012 | Tsuchiya et al. |
| 8,225,453 B2 | 7/2012 | Yamada |
| 8,245,349 B2 | 8/2012 | Tsuchiya et al. |
| 8,435,625 B2 | 5/2013 | Ruehe et al. |
| 8,528,151 B2 | 9/2013 | Przepasniak |
| 8,536,074 B2 | 9/2013 | Fereshtehkhou et al. |
| 8,617,685 B2 | 12/2013 | Yamada |
| 8,646,144 B2 | 2/2014 | Wada et al. |
| 8,752,232 B2 | 6/2014 | Otsuka et al. |
| 8,756,746 B2 | 6/2014 | Policicchio |
| 8,763,197 B2 | 7/2014 | Policicchio et al. |
| 8,793,832 B2 | 8/2014 | Yamada |
| 8,851,776 B2 | 10/2014 | Schwarz et al. |
| 8,858,971 B2 | 10/2014 | Rao |
| 9,113,768 B2 | 8/2015 | Wada et al. |
| 9,198,553 B2 | 12/2015 | Policicchio |
| 9,204,775 B2 | 12/2015 | Pung et al. |
| 9,296,176 B2 | 3/2016 | Escaffre et al. |
| 9,339,165 B2 | 5/2016 | Vetter et al. |
| 9,622,943 B2 | 4/2017 | Scala et al. |
| 10,076,583 B2 | 9/2018 | Lynch |
| 10,143,764 B2 | 12/2018 | Lynch |
| 10,383,825 B2 | 8/2019 | Lebo et al. |
| 10,821,056 B2 | 11/2020 | Swartz et al. |
| 10,835,455 B2 | 11/2020 | Payne et al. |
| 10,932,996 B2 | 3/2021 | Baig et al. |
| 11,812,909 B2 | 11/2023 | Lynch |
| 2001/0048933 A1 | 12/2001 | L'Alloret |
| 2002/0160088 A1 | 10/2002 | Sakaguchi et al. |
| 2003/0021760 A1 | 1/2003 | Kumar et al. |
| 2003/0053980 A1 | 3/2003 | Dodd et al. |
| 2004/0185011 A1 | 9/2004 | Alexander |
| 2005/0152851 A1 | 7/2005 | Kaminski |
| 2006/0024245 A1 | 2/2006 | Gebreselassie et al. |
| 2009/0155190 A1 | 6/2009 | Gebreselassie et al. |
| 2010/0061941 A1 | 3/2010 | Gebreselassie |
| 2011/0027328 A1 | 2/2011 | Baig et al. |
| 2011/0053826 A1 | 3/2011 | Wise |
| 2011/0262507 A1 | 10/2011 | Spring |
| 2013/0111682 A1 | 5/2013 | Pung |
| 2013/0302385 A1 | 11/2013 | Muenz et al. |
| 2014/0289984 A1 | 10/2014 | Vetter |
| 2015/0196185 A1 | 7/2015 | Fiske |
| 2015/0313803 A1 | 11/2015 | Lynch et al. |
| 2015/0313808 A1 | 11/2015 | Lynch et al. |
| 2016/0051684 A1 | 2/2016 | Wang |
| 2016/0120771 A1 | 5/2016 | Simonet et al. |
| 2016/0346175 A1 | 12/2016 | Sasik et al. |
| 2018/0127692 A1 | 5/2018 | Coope-Epstein et al. |
| 2019/0160022 A1 | 5/2019 | Chiou |
| 2019/0298625 A1 | 10/2019 | Hilliard, Jr. et al. |
| 2019/0343732 A1 | 11/2019 | Mao |
| 2020/0000693 A1 | 1/2020 | Traynor et al. |
| 2021/0007940 A1 | 1/2021 | Swartz et al. |

FOREIGN PATENT DOCUMENTS

| | | |
|---|---|---|
| DE | 202007001353 U1 | 5/2007 |
| EP | 0916722 A2 | 5/1999 |
| EP | 2465487 A2 | 6/2012 |
| EP | 2170257 B1 | 11/2012 |
| ES | 2548699 T3 | 10/2015 |
| GB | 2221389 A | 2/1990 |
| WO | 9209679 A1 | 6/1992 |
| WO | 0196461 A1 | 12/2001 |
| WO | 03075735 A1 | 9/2003 |
| WO | 2007133265 A2 | 11/2007 |
| WO | 2009095891 A1 | 8/2009 |
| WO | 2010060653 A2 | 6/2010 |
| WO | 2014124066 A1 | 8/2014 |

OTHER PUBLICATIONS

PCT Search Report and Written Opinion for PCT/US2021/026301 dated Jul. 5, 2021.
All Office Actions, U.S. Appl. No. 17/196,379.
All Office Actions, U.S. Appl. No. 17/225,146.
All Office Actions, U.S. Appl. No. 17/225,148.
All Office Actions, U.S. Appl. No. 17/225,150.
All Office Actions, U.S. Appl. No. 17/225,151.
All Office Actions, U.S. Appl. No. 17/225,153.
All Office Actions, U.S. Appl. No. 17/225,176.
All Office Actions, U.S. Appl. No. 17/225,218.
Clinton D. Stevenson, et al.,"Capillary Pressure as Related to Water Holding in Polyacrylamide and Chicken Protein Gels", Journal of Food Science, vol. 78, Nr. 2, dated 2013,pp. C145-C151.
F. V. Ryer, Oil & Soap, "Research Laboratory, Lever Brothers Company Cambridge, Massachusetts", dated Oct. 1946, pp. 310-313.
F. V. Ryer, et al. Growing Single Crystals, "A Method of Growing Single Crystals of Sodium Stearate and Sodium Palmitate", dated Feb. 4, 1944, pp. 154-158.
Marc N. G. de Mul, et al. Langmuir 2000, "Solution Phase Behavior and Solid Phase Structure of Long-Chain Sodium Soap Mixtures", vol. 16, No. 22, dated 2000, pp. 8276-8284.
Masao Sambuichi, et al. Dewatering of Gels, "Filtration, Food Chemical Engineering, Solid Liquid Separation, Dewatering, Expression, Gel", Journal of Chemical Engineering of Japan, vol. 27, No. 5, dated 1994, pp. 616-620.
Matthew L Lynch, Acid-soaps, "The study of acid-soap crystals has resulted in many conflicting data", Current Opinion in Colloid & Interface Science, dated 1997,pp. 495-500.
Matthew L. Lynch, et al. Acid-soap crystals, "Spectroscopic and Thermal Characterization of 1:2 Sodium Soap/Fatty Acid Acid-Soap Crystals", J. Phys. Chem., vol. 100, No. 1, 1996, pp. 357-361.
Matthew L. Lynch, Structure of Fatty Acid-Soap Crystals,"Intermolecular Interactions and the Structure of Fatty Acid-Soap Crystals", J. Phys. Chem. B, vol. 105, No. 2, dated 2001, pp. 552-561.
Theodore P. Labuza, et al. , "Measurement of Gel Water-Binding Capacity by Capillary Suction Potential", Journal of Food Science, vol. 43, dated 1978 ,pp. 1264-1269.
Unpublished U.S. Appl. No. 17/196,379, filed Mar. 9, 2021, to first inventor Geoffrey Marc Wise.
Unpublished U.S. Appl. No. 17/225,150, filed Apr. 8, 2021, to first inventor Matthew Lawrence Lynch et. al.
Unpublished U.S. Appl. No. 17/225,218, filed Apr. 8, 2021, to first inventor Matthew Lawrence Lynch et. al.
Unpublished U.S. Appl. No. 17/225,147, filed Apr. 8, 2021, to first inventor Matthew Lawrence Lynch. et al.
Unpublished U.S. Appl. No. 17/225,151, filed Apr. 8, 2021, to first inventor Matthew Lawrence Lynch et. al.
Unpublished U.S. Appl. No. 17/225,153, filed Apr. 8, 2021, to first inventor Matthew Lawrence Lynch et. al.
Unpublished U.S. Appl. No. 17/225,176, filed Apr. 8, 2021, to first inventor Matthew Lawrence Lynch et. al.
Unpublished U.S. Appl. No. 17/225,148, filed Apr. 8, 2021, to first inventor Matthew Lawrence Lynch et. al.
All Office Actions; U.S. Appl. No. 17/485,906, filed Sep. 27, 2021.
Unpublished U.S. Appl. No. 17/485,906, filed Sep. 27, 2021, to first inventor et. al.
All Office Actions; U.S. Appl. No. 18/450,176, filed Aug. 15, 2023.
Unpublished U.S. Appl. No. 18/450,176, filed Aug. 15, 2023, to Matthew Lawrence Lynch et. al.

(56) References Cited

OTHER PUBLICATIONS

All Office Actions; U.S. Appl. No. 18/909,337, filed Oct. 8, 2024.
All Office Actions; U.S. Appl. No. 18/909,342, filed Oct. 8, 2024.
Unpublished U.S. Appl. No. 18/909,337, filed Oct. 8, 2024, Matthew Lawrence Lynch et al.
Unpublished U.S. Appl. No. 18/909,342, filed Oct. 8, 2024, Matthew Lawrence Lynch et al.

* cited by examiner

RHEOLOGICAL SOLID ORAL COMPOSITION

FIELD OF THE INVENTION

Rheological solid oral composition comprising more than about 80% water having a crystallizing agent with an elongated, fiber-like crystal habit. Wherein the rheological solid oral composition exhibits properties of sufficient firmness, low surface adhesion, aqueous phase expression, and thermal stability critical for dosing of oral active agents.

BACKGROUND OF THE INVENTION

The generally accepted method of pharmaceutical and nutraceutical delivery is through the use of oral dosages, usually solids, with the active agents being in pill or capsule form. However, many individuals have a difficult time swallowing the pills. This can be due to age, lack of lubricating fluids, gag reflex, size of the pill, potential lodging of the pill in a user's throat or the general taste of the pill.

To address the difficulty that many people have in swallowing pills, efforts to develop and employ pill enveloping or coating materials have been undertaken. In many cases, those efforts have resulted in pills that are made in the form of capsules and gel-caps, which have a smooth, but dry, outer surface. This surface dryness can still lead to a pill adhering to portions of a user's oral cavity or even the throat or esophagus. One effort to overcome this disadvantage has been application of coatings that reduce the adhesion properties of the pill upon contact with moisture, however for this to work there is often a minimum amount of moisture and time required for the coating to "activate." This additional residence time in a user's oral cavity often with the pill adhered to the user's tongue can cause discomfort from both a texture and taste aspect.

A substantial proportion of adults have difficulty swallowing traditional pills thereby creating the need for an alternate "solid" dose form that is easier to swallow. What is needed is an easy to use and swallow oral composition, such as those of the present invention, which have low surface adhesion (are self-lubricating), facilitating consumption, and ease of swallowing.

SUMMARY OF THE INVENTION

A rheological solid oral composition for delivering an oral active agent that comprises a crystallizing agent comprising a salt of fatty acids containing from about 13 to about 20 carbon atoms; an aqueous phase; and an oral active agent.

A rheological solid oral composition for delivering an oral active agent that comprises a crystallizing agent comprising a salt of fatty acids containing from about 13 to about 20 carbon atoms; an aqueous phase; and an oral active agent; wherein, the rheological solid oral composition has a firmness between about 0.1 N to about 50.0 N as determined by the FIRMNESS TEST METHOD; a thermal stability of about 40° C. to about 95° C. as determined by the THERMAL STABILITY TEST METHOD; a liquid expression of between about 100 J m-3 to about 8,000 J m-3 as determined by the AQUEOUS PHASE EXPRESSION TEST METHOD; and wherein the oral active agent is at least one of Antacids, H2 Antagonists, Proton Pump Inhibitors, Anesthetics, Antibiotics, Anticholinergics, Antihistamines, Antitussives, Antivirals, Decongestants, Demulcents, Expectorants, Mucolytics, Pain-Relieving Agents, Sleep Agents, or Dietary Supplements.

BRIEF DESCRIPTION OF THE DRAWINGS

While the specification concludes with claims particularly pointing out and distinctly claiming the subject matter that is regarded as the present disclosure, it is believed that the disclosure will be more fully understood from the following description taken in conjunction with the accompanying drawings. Some of the figures may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. None of the drawings are necessarily to scale.

DETAILED DESCRIPTION OF THE INVENTION

Figure 1:
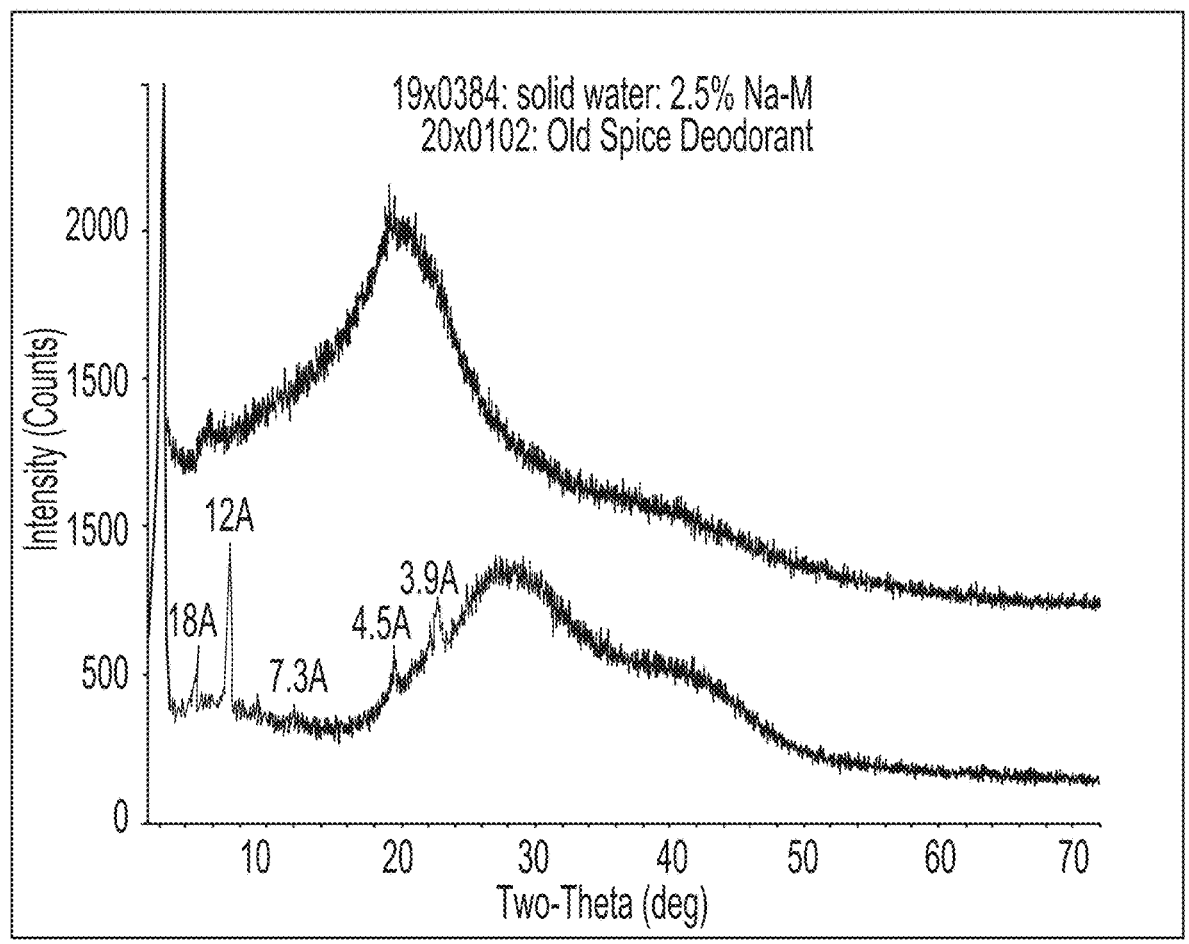
FIG. 1. X-ray Diffraction Pattern
FIG. 2. SEM of Interlocking Mesh
FIG. 3. Inventive Phase Diagram of Sodium Hexadecanoate and Acetaminophen
FIG. 4. Inventive Phase Diagram of Sodium Hexadecanoate and Diphenhydramine

The present invention provides a rheological solid oral composition comprising a crystalline mesh. The crystalline mesh ("mesh") comprises a relatively rigid, three-dimensional, interlocking crystalline skeleton framework of fiber-like crystalline particles (formed from crystallizing agents), having voids or openings containing aqueous solution and one or more oral active agents. The mesh provides a self-supporting structure, such that a rheological solid oral composition may 'stand on its own' when resting on a surface. The rheological solid oral composition has a surface with low surface adhesion and low coefficient of friction, such that the composition can be slippery when compressed having a static coefficient of friction of preferably less than about 0.50, more preferably less than about 0.30 and most preferably less than 0.10, and a dynamic coefficient of friction of preferably less than about 0.50, more preferably less than about 0.30 and most preferably less than 0.10. Further, if compressed above a critical stress, the mesh allows the rheological solid oral composition to express the entrapped aqueous phase, and oral active agents. The rheological solid oral compositions of the present invention include crystallizing agent(s), aqueous phase and at least one oral active agent.

Rheological solid oral compositions, in the form of a pill or coating on a solid pill, are self-lubricating, thus facilitating consumption and ease of swallowing. In another aspect, the rheological solid oral compositions can enable an easily chewed dosage form, where the liquid is expressed for subsequent ingestion as a liquid. In yet another aspect, rheological solid oral compositions can enable rapid oral dissolution and buccal delivery/mucosal absorption of certain ingredients. In some cases, buccal delivery can be/is preferred as those ingredients may be rendered unavailable by normal gastric and intestinal processes.

It is surprising that it is possible to prepare rheological solid oral compositions that exhibit sufficient firmness, aqueous phase expression and thermal stability. Not wishing to be bound by theory, it is believed that sodium carboxylates present in high-water compositions (e.g. above about 80%) and correct chain length purity may form elongated, fiber-like crystal habits. These crystals form mesh structures that result in rheological solid oral compositions even at very low concentrations. Firmness may be achieved by carefully adjusting the concentration and chain length distribution of the crystallizing agent. Aqueous phase expression may be achieved from these rheological solid structures, by compression above a yield behavior that breaks the mesh structure allowing water and dissolved or suspended actives to flow from the composition. One skilled in the art recognizes this as a plastic deformation of the mesh structure. This stands in contrast to other gelling agents like gelatin, that can be formulated at very high-water concentrations but do not express water with compression. Thermal Stability may be achieved by ensuring the proper chain length and chain length distributions to ensure the mesh does not solubilize until heated above 40° C. This is an important property in relation to the shelf-life and supply chain for consumer products. Addition of sodium chloride can be used to increase the thermal stability of the composition but should be added correctly to ensure the proper formation of the mesh. These discovered design elements stand in contrast to compositions prepared with too-soluble a gelling agent to be practically thermal stable. Finally, such rheological solid oral compositions are prepared by gradually cooling the mixture in contrast to rapid freezing or other mechanically invasive processes. Not wishing to be bound by theory, passive processes allow the formation of very large and efficient fibrous crystals rather the breaking them into smaller less efficient crystals.

Crystallizing Agent(s)

In the present invention the mesh of a rheological solid oral composition includes fiber-like crystalline particles formed from crystallizing agents; wherein "Crystallizing agent" as used herein includes sodium salts of fatty acids with shorter chain length (from about C13 to about C20 or from about C13 to about C18 or from about C13 to about C16 or from about C13 to about C14), such as sodium palmitate (C16). Commercial sources of crystallizing agent usually comprise complicated mixtures of molecules, often with chain lengths between C10 to C22. The rheological solid oral compositions are best achieved with a 'narrow blend'—or distribution of crystallizing agent chain lengths, further best achieved with blends in the absence of very short chain lengths (C12 or shorter) and measurable amounts of unsaturation on the chains of the fatty acid sodium salts, and best achieved with a single chain length between C13 to C20, coupled with controlled crystallizing processing. Accordingly, rheological solid oral compositions are best achieved when the blend of the chain length distribution is preferably greater than about Po>0.3, more preferably about Po>0.5, more preferably about Po>0.6, more preferably about Po>0.7 and most preferably about Po>0.8, as determined by the BLEND TEST METHOD. Po describes the total weight fraction of optimal chain length molecules of crystallizing agent to the total weight of crystallizing agent molecules. One skilled in the art, recognizes crystalline particles as exhibiting sharp scattering peaks between 0.25-60 deg. 2θ in powdered x-ray diffraction measurements. This is in sharp contrast to compositions in which these materials are used as gelling agents, which show broad amorphic scattering peaks emanating from poorly formed solids which lack the long-range order of crystalline solids (FIG. 1).

Figure 2:
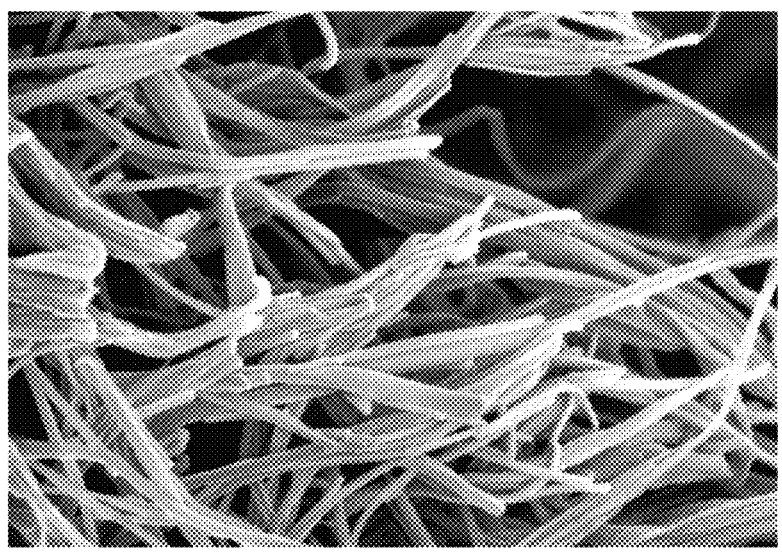

Rheological solid oral compositions comprise greater than about 80% water and are 'structured' by a mesh of interlocking, fiber-like crystalline particles of mostly single-chain length, as described above, see (FIG. 2). The term 'fiber-like crystalline particle' refers to a particle in which the length of the particle in the direction of its longest axis is greater than 10× the length of the particle in any orthogonal direction. The fiber-like crystalline particles produce a mesh at very low concentrations (~0.5 wt %) which creates a solid that yields only with a minimum applied stress—i.e. rheological solid. The aqueous phase primarily resides in the open spaces of the mesh. In preparing these compositions, the crystallizing agent is dissolved in aqueous phase using heat. The fiber-like crystalline particles form into the mesh as the mixture cools over minutes to hours.

Such compositions exhibit three properties used to make effective consumer product for envisioned applications:

Aqueous Phase Expression

Aqueous phase expression is an important property for consumer applications in the present invention, expressed in work to express water per unit volume, where preferred compositions are between 300 J m-3 and about 9,000 J m-3, more preferably between 1,000 J m-3 and about 8,000 J m-3, more preferably between 2,000 J m-3 and about 7,000 J m-3 and most preferably between 2,500 J m-3 and about 6,000 J m-3, as determined by the AQUEOUS PHASE EXPRESSION TEST METHOD. These limits allow for viable product compositions that—for example, provide evaporative and/or sensate-based cooling and easy swallowing when the composition is consumed. These work limits are in contrast to compositions that do not express aqueous phase when compressed, such as gelatins. So, it is surprising that high-water compositions can be created with these materials, that express aqueous phase with compression. Not wishing to be bound by theory, it is believed this a result of a network of crystalline materials that break up during the application of sufficient stress—releasing the aqueous phase with no uptake when the compression is released.

Firmness

Firmness should be agreeable to consumer applications, in forming a structured rheological solid oral composition, with preferred embodiments between about 0.5 N to about 25.0 N, more preferably between 1.0 N to about 20.0 N, more preferably between 3.0 N to about 15.0 N and most preferably between 5.0 N and about 10.0 N. These firmness values allow for viable product compositions that may retain their shape when resting on a surface, and as such are useful as a rheological solid stick to provide a dry-to-the-touch but wet-to-the-push properties. The firmness values are significantly softer than bar soaps and deodorants, which exceed these values. So, it is surprising that high-water compositions can be created that remain as rheological solid oral compositions with between about 0.25 wt % to about 10 wt % crystallizing agent, more preferably between about 0.5 wt % to about 7 wt % crystallizing agent and most preferably between about 1 wt % to about 5 wt % crystallizing agent. Not wishing to be bound by theory, it is believed this a result of crystallizing agent materials creating the interlocking mesh that provides sufficient firmness.

Thermal Stability

Thermal stability is used to ensure that the structured rheological solid oral composition can be delivered as intended to the consumer through the supply chain, preferably with thermal stability greater than about 40° C., more preferably greater than about 45° C. and most preferably greater than about 50° C., as determined by the THERMAL STABILITY TEST METHOD. Creating compositions with acceptable thermal stability is difficult, as it may vary unpredictably with concentration of the crystallizing agent and soluble active agent(s). Not wishing to be bound by theory, thermal stability results from the insolubility of the crystallizing agent in the aqueous phase. Conversely, thermal instability is thought to result from complete solubilization of the crystallizing agent that comprised the mesh.

Chain Length Blends

Effective chain length blends allow the creation of effective mesh microstructures in rheological solid oral compositions. In fact, adhoc (or informed selection) of crystallizing agents often leads to liquid or very soft compositions. The crystallizing agent may comprise a mixture of sodium carboxylate molecules, where each molecule has a specific chain length. For example, sodium stearate has a chain length of 18, sodium oleate has a chain length of 18:1 (where the 1 reflects a double bond in the chain), sodium palmitate has a chain length of 16, and so on. The chain length distribution—or the quantitative weight fraction of each chain length in the crystallizing agent, can be determined by the BLEND TEST METHOD, as described below. Commercial sources of crystallizing agent usually comprise complicated mixtures of molecules, often with chain lengths between 10 to 22.

Rheological solid oral compositions of the present invention have preferred chain length blends, as described by 'Optimal Purity' (Po) and 'Single Purity' (Ps), determined by the BLEND TEST METHOD. Sodium carboxylate crystallizing agents can have an 'Optimal Chain Length' of between 13 to 22 carbons and can be used alone or combined to form mesh structures that satisfy all three performance criteria of a rheological solid oral composition. Not wishing to be bound by theory, it is believed that these chain length molecules (13 to 22) have a high solubilization temperature (e.g. Krafft Temperature) and can pack into crystals efficiently. Sodium carboxylate crystallizing agents can have 'Unsuitable Chain Length' crystallizing agents have chain length of sodium carboxylate molecules of 10, 12, 18:1 and 18:2 (and shorter or other unsaturated chain lengths). When present in compositions alone or in some combinations with 'optimal chain length' molecules, they do not form rheological solid oral composition that meet the required performance criteria. Accordingly, inventive compositions require the proper blend of crystallizing agent molecules, to ensure the proper properties of the rheological solid oral composition. Po describes the total weight fraction of optimal chain length molecules of crystallizing agent to the total weight of crystallizing agent molecules, that is preferably Po>0.4, more preferably Po>0.6, more preferably Po>0.8 and most preferably Po>0.90. Ps describes the total weight fraction of the most common chain length molecule in the crystallizing agent to the total weight of crystallizing agent, that is preferably Ps>0.5, more preferably Ps>0.6, more preferably Ps>0.7, more preferably Ps>0.9.

Aqueous Phase

The rheological solid oral composition may include an aqueous carrier. The aqueous carrier which is used may be distilled, deionized, or tap water. Water may be present in any amount for the rheological solid oral composition to be an aqueous solution. Water may be present in an amount of about 80 wt % to 99.5 wt %, alternatively about 90 wt % to about 99.5 wt %, alternatively about 92 wt % to about 99.5 wt %, alternatively about 95 wt %, by weight of the rheological solid oral composition. Water containing a small amount of low molecular weight monohydric alcohols, e.g., ethanol, methanol, and isopropanol, or polyols, such as ethylene glycol and propylene glycol, can also be useful. However, the volatile low molecular weight monohydric alcohols such as ethanol and/or isopropanol should be limited since these volatile organic compounds will contribute both to flammability problems and environmental pollution problems. If small amounts of low molecular weight monohydric alcohols are present in the rheological solid oral composition due to the addition of these alcohols for solubilizing flavors or stabilizers for some preservatives, the level of monohydric alcohol may about 1 wt % to about 5 wt %, alternatively less than about 6 wt %, alternatively less than about 3 wt %, alternatively less than about 1 wt %, by weight of the rheological solid oral composition.

However, other components can be optionally dissolved with the low molecular weight monohydric alcohols in the water to create an aqueous phase. Combined, these components are referred to as soluble active agents. Such soluble active agents include, but are not limited to, catalysts, activators, peroxides, enzymes, antimicrobial agents, preservatives, sodium chloride, surfactants, polyols, and water soluble Antacids, H2 Antagonists, Proton Pump Inhibitors, Anesthetics, Antibiotics, Anticholinergics, Antihistamines, Antitussives, Antivirals, Decongestants, Demulcents, Expectorants, Mucolytics, Pain-Relieving Agents, Sleep Agents, Probiotics, vitamins, minerals, or Dietary Supplements. The crystallizing agent and insoluble active agents, including water insoluble water soluble Antacids, H2 Antagonists, Proton Pump Inhibitors, Anesthetics, Antibiotics, Anticholinergics, Antihistamines, Antitussives, Antivirals, Decongestants, Demulcents, Expectorants, Mucolytics, Pain-Relieving Agents, Sleep Agents, Probiotics, vitamins, minerals, or Dietary Supplements, may be dispersed in the aqueous phase.

Preservatives

In embodiments, soluble active agent can include a preservative. The preservative may be present in an amount sufficient to prevent spoilage or prevent growth of inadvertently added microorganisms for a specific period of time, but not sufficient enough to contribute to the odor neutralizing performance of the rheological solid oral composition. In other words, the preservative is not being used as the antimicrobial compound to kill microorganisms on the surface onto which the rheological solid oral composition is deposited. Instead, it is being used to prevent spoilage of the rheological solid oral composition in order to increase the shelf-life of the rheological solid oral composition.

The following are non-limiting examples of preservatives that may be used in a rheological solid oral composition: Neem Oil, salt (sodium chloride), lemon, and honey, benzoates such as sodium benzoate, sorbates, propionates, and nitrites or combinations thereof.

Solvents

The composition can contain a solvent. Non-limiting examples of solvents can include ethanol, glycerol, propylene glycol, polyethylene glycol 400, polyethylene glycol 200, and mixtures thereof. In one example the composition comprises from about 0.5% to about 15% solvent, in another example from about 1.0% to about 10% solvent, and in another example from about 1.0% to about 8.0% solvent, and in another example from about 1% solvent to about 5% solvent.

Sodium chloride (and other sodium salts) is a particular useful additive to the aqueous phase to adjust the thermal stability of compositions but must be added into the composition with particular care (Example 3). Not wishing to be bound by theory, sodium chloride is thought to 'salt out' inventive crystallizing agents decreasing their solubility. This has the effect of increasing the thermal stability temperature of the rheological solid oral composition as measured by the THERMAL STABILITY TEST METHOD. For example, Optimal Chain Length crystallizing agents can have the thermal stability temperatures increased as much as 15° C. with sodium chloride addition. This is particularly valuable as the addition of other ingredients into the aqueous phase often lower the thermal stability temperature in the absence of sodium chloride. Surprisingly, adding sodium chloride can lead to adverse effects in the preparation of the rheological solid oral compositions. It is preferable in most making processes, to add sodium chloride into the hot crystallizing agent aqueous phase before cooling to form the mesh. However, adding too much may cause 'curding' of the crystallizing agents and unacceptable compositions. The sodium chloride may also be added after the formation of the mesh, to provide the benefit of raising the thermal stability temperature at higher levels without curding. Finally, while the thermal stability temperature is increased with addition of sodium chloride, the addition of other non-sodium salts changes the fibrous nature of the crystals formed from the crystallizing agents, to form plates or platelet crystals, which are not rheological solids.

Flavors, Sweeteners, Colors and Coolants

The following classes of compounds may be used in a rheological solid oral composition to improve the appearance, flavor and/or sensory experience of rheological solid oral composition.

Flavors

U.S. Pat. No. 10,322,144 discloses non-limiting examples of flavors that can include natural flavoring agents, artificial flavoring agents, artificial extracts, natural extracts and combinations thereof. Non-limiting examples of can include vanilla, honey, lemon, lemon honey, cherry vanilla, peach, honey ginger, chamomile, cherry, cherry cream, mint, vanilla mint, dark berry, black berry, raspberry, peppermint, spearmint, honey peach, acai berry, cranberry, honey cranberry, tropical fruit, dragon fruit, wolf berry, red stem mint, pomegranate, black current, strawberry, lemon, lime, peach ginger, orange, orange cream, cream sickle, apricot, anethole, ginger, jack fruit, star fruit, blueberry, fruit punch, lemon grass, chamomile lemon grass, lavender, banana, strawberry banana, grape, blue raspberry, lemon lime, coffee, espresso, cappuccino, honey, wintergreen mint, bubble gum, tart honey lemon, sour lemon, sour cherry, green apple, boysenberry, rhubarb, strawberry rhubarb, persimmon, green tea, black tea, red tea, white tea, honey lime, cherry lime, apple, tangerine, grapefruit, kiwi, pear, vanillin, ethyl vanillin, maltol, ethyl-maltol, pumpkin, carrot cake, white chocolate raspberry, chocolate, white chocolate, milk chocolate, dark chocolate, chocolate marshmallow, apple pie, cinnamon, hazelnut, almond, cream, crème brûlée, caramel, caramel nut, butter, butter toffee, caramel toffee, aloe vera, whiskey, rum, cocoa, licorice, pineapple, guava, melon, watermelon, elder berry, oral cavity cooler, raspberries and cream, peach mango, tropical, cool berry, lemon ice, nectar, spicy nectar, tropical mango, apple butter, peanut butter, tangerine, tangerine lime, marshmallow, cotton candy, apple cider, orange chocolate, citral, denatonium benzoate, ethyl maltol, malic acid, menthol, and combinations thereof Sweeteners The following sweeteners are disclosed in U.S. Pat. No. 6,391,886, sweeteners may be selected from the group consisting of sodium saccharine or 1,2-benzisothiazol-3 (2H)-one 1,1-dioxide, available as Sweetmate® from The NutraSweet Company, potassium acesulfame or 6-methyl-1,2,3-oxathiazin-4(3H)-15 one 2,2-dioxide, available as Sunett® from Nutrinova Company, sucralose or 1',4,6'-trichloro-galactosucrose, available as Splenda® from McNeil Specialty Products Company, aspartame or N-L-alpha-aspartyl-Lphenylalanine 1-methyl ester, available as NutraSweet® or 20 Equal® from The NutraSweet Company, monoammonium glycyrrhizinate, neohesperidin dihydrochalcone (NHDC), thaumatin, a basic protein extracted from the fruit of the tropical plant, Thaumatocous danielli, available as Talin® from The Talin Food Company, and mixtures thereof Coolants As disclosed in U.S. Pat. No. 6,391,886, Coolants may be selected from the group consisting, but not limited to: menthol, the class of carboxamides, preferably N-ethyl-pmenthane-3-carboxamide and N,2,3-trimethyl-2-isopropylbutanamide available as WS-3 and WS-23 respectively, both from Millennium Specialty Chemicals; 1-menthone-/d-iso-menthone glycerin ketal and menthyl lactate available as MGA and Frescolt® respectively from Haarmann and Reimer; 3-1-menthoxypropane-1,2-diol available as TK-10® from Takasago Perfumery Co., Tokyo, Japan, menthyl acetoacetate available as Novillone® from Noville, mono menthyl succinate available as Physcool® from Mane and Optacool® from Haarmann and Reimer, and Coolant 3, Coolant 4 & Coolant 5, from International Flavors & Fragrances Colors As described in U.S. Pat. No. 9,421,171, colorants may be natural or synthetic dyes and pigments selected from the group consisting of, but not limited to: organic dyes and their lakes, iron oxide pigments, titanium dioxide, talc, anthocyanins, carmine, riboflavin, and mixtures thereof. In one example, the solid dosage form does not comprise synthetic dyes or synthetic pigments.

Oral Active Agents (Actives)

The rheological solid oral composition may be used to deliver the following classes of Oral Active Agents (Actives):

An oral active agent is any component that provides pharmacological activity or other direct effect in the diagnosis, cure, mitigation, treatment, or prevention of disease, or to affect the structure or any function of the body of man or animals.

Oral active agents can include a great many ingredients/compounds and may be used for a wide array of conditions as either prescription, Over The Counter (OTC) or Dietary Supplement products. In some compositions, natural/botanical ingredients may be considered the primary oral active agent or utilized in addition to oral active agents. The following are non-limiting examples of oral active agents and would include pharmaceutically acceptable salts, metabolites and combinations thereof.

Antacids and gastrointestinal treatments including H2 Antagonists and Proton Pump Inhibitors: Non-limiting examples of actives that occur in antiacid products include alginic acid and alginate salts, aluminum hydroxide, bismuth subsalicylate, calcium carbonate, famotidine, magnesium carbonate, magnesium hydroxide, magnesium trisilicate, loperamide, cimetidine, ranitidine, nizatidine, omeprazole, pantoprazole, lansoprazole, simethicone and combinations thereof.

Anesthetics

Non-limiting examples of anesthetics can include phenol, menthol, dyclonine HCl, benzocaine, lidocaine, hexylresorcinol, and combinations thereof.

Antibiotics

As disclosed in U.S. Pat. No. 9,421,171, Non-limiting examples of antibiotics include nitroimidazole antibiotics, tetracyclines, penicillin-based antibiotics such as amoxicillin, cephalosporins, carbopenems, aminoglycosides, macrolide antibiotics, lincosamide antibiotics, 4-quinolones, fluoroquinolones, rifamycins, macrolides, nitrofurantoin, and combinations thereof.

Anticholinergics

Non-limiting examples anticholinergics can include ipratropium, chlorpheniramine, brompheniramine, diphenhydramine, doxylamine, clemastine, triprolidine, and combinations thereof.

Antihistamines

Non-limiting examples of antihistamines can include chlorpheniramine, desloratadine, levocetirizine, diphenhydramine, doxylamine succinate, triprolidine, clemastine, pheniramine, brompheniramine, dexbrompheniramine, loratadine, cetirizine, fexofenadine, amlexanox, alkylamine derivatives, cromolyn, acrivastine, ibudilast, bamipine, ketoprofen, nedocromil, omalizumab, dimethindene, oxatomide, pemirolast, 10 pyrrobutamine, penfigetide, thenaldine, picumast, tolpropamine, ramatroban, repirinast, suplatast tosylate aminoalkylethers, tazanolast, bromodiphenhydramine, tranilast, carbinoxamine, traxanox, chlorphenoxamine, diphenylpyaline, embramine, p-methyldiphenhydramine, moxastine, orphenadrine, phenyltoloxamine, setastine, ethylenediamine derivatives, chloropyramine, chlorothen, methapyrilene, pyrilamine, talastine, thenyldiamine, thonzylamine 15 hydrochloride, tripelennamine, piperazines, chlorcyclizine, clocinizine, homochlorcyclizine, hydroxyzine, tricyclics, phenothiazines, mequitazine, promethazine, thiazinamium methylsulfate, azatadine, cyproheptadine, deptropine, isothipendyl, olopatadine, mpatadine, antazoline, astemizole, azelastine, bepotasfine, clemizole, ebastine, emedastine, epinastine, levocabastine, mebhydroline, mizolastine, phenindamine, terfenadine, tritoqualine, and combinations thereof;

Antitussives

Non-limiting examples of antitussives (i.e. cough suppressants) can include dextromethorphan, menthol, codeine, chlophedianol, levodropropizine, and combinations thereof.

Antivirals

Non-limiting examples of anti-virals can include amanUdine, rimantadine, pleconaril, zanamivir, oseltamivir, and combinations thereof.

Decongestants

Non-limiting examples of decongestants can include pseudoephedrine, pseudoephedrine hydrochloride, phenylephrine, phenylephrine hydrochloride, phenylpropanolamine, naphazoline, 1-desoxyephedrine, ephedrine, propylhexedrine, and combinations thereof;

Demulcents

Non-limiting examples of demulcents can include glycerin, honey, pectin, gelatin, slippery elm bark, liquid sugar, glycyrrhizin (licorice), and combinations thereof.

Expectorants

Non-limiting examples of expectorants can include guaifenesin, ambroxol, bromhexine, and combinations thereof;

Mucolytics

As disclosed in U.S. Pat. No. 9,421,171, non-limiting examples of mucolytics can include ambroxol, N-acetylcysteine, bromhexine, and combinations thereof Pain-Relieving Agents Non-limiting examples of pain relievers, can include acetaminophen, ibuprofen, ketoprofen, diclofenac, naproxen, aspirin, and combinations thereof, as well as prescription analgesics, non-limiting examples of which include propyxhene HCl, codeine, mepridine, and combinations thereof.

Sleep Agents

Non-limiting examples of sleep actives include: zolpidem estazolam, eszopiclone, suvorexant, butabarbitol, flurazepam and quazepam.

Dietary Supplements (commonly called Vitamins-Minerals-Supplements (VMS))

US law defines dietary supplements in part as products taken by mouth that contain a "dietary ingredient." Dietary ingredients include vitamins, minerals, amino acids, and herbs or botanicals, as well as other substances that can be used to supplement the diet. Dietary supplements come in many forms, including tablets, capsules, powders, energy bars, and liquids. These products are available in stores throughout the United States, as well as on the Internet. They are labeled as dietary supplements and include among others vitamin and mineral products "botanical" or herbal products—These come in many forms and may include plant materials, algae, macroscopic fungi, or a combination of these materials. Amino acid products—Amino acids are known as the building blocks of proteins and play a role in metabolism.

enzyme supplements—Enzymes are complex proteins that speed up biochemical reactions.

Dietary Supplement Ingredients or Benefit Areas

Allergy Supplement Ingredients

Non-limiting examples of natural or botanical ingredients that are marketed toward allergy include vitamin C, butterbur, bromelain, probiotics (spore-forming and non-spore totaling); and quercetin.

Antioxidant Supplement Ingredients

Non-limiting examples of antioxidants include: vitamins C and selenium, and carotenoids, such as beta-carotene, lycopene, lutein, and zeaxanthin.

Digestive Wellness/Gastrointestinal Ingredients Including Dietary Fibers

Non-limiting examples of natural or botanical ingredients marketed for digestive or gastroinstinal support include: apple cider vinegar, licorice, ginger, chamomile, marshmallow, slippery elm, Boswellia, aloe vera, peppermint oil, dietary fibers such as psyllium husk, inulin, cellulose, guar gum, pectin, locust bean gum, hydroxyproplymethylcellulose, mixed plant cell wall fibers, arabinoxylan, alginate, galactooligosaccharides, polydextrose, resistant maltodextrin/dextrin, glucomannan, prebiotics, probiotics, various enzymes or combinations thereof.

Enzymes

Non-limiting examples of enzymes as dietary supplements include: bromelain, *papaya*, lactase, amylase, pancreatin, lipase, and pepsin.

Immunity Agents

Non-limiting examples of ingredients that allege to support immunity include: ashwagandha, elderberry, holy basil, moringa, and turmeric, probiotics (including fermentates such as EpiCor®) or combinations thereof.

Metabolics

Non-limiting examples of marketed ingredients include: alpha-lipoic acid, apple cider vinegar, creatine, chromium, garcinia, glucomannan, magnesium, omega-3 fatty acids, vitamins C and D, and cinnamon.

Vitamins and Minerals

Non-limiting examples of vitamins minerals that appear in dietary supplements include: calcium, magnesium, selenium, chromium, zinc, copper, iron, iodine, phosphorous, potassium, sodium; vitamins A, B1, B2, B5, B6, B7, B9, B12, C, D, and E.

Neurologics

Non-limiting examples of ingredients marketed for nerve health include: alpha lipoic acid, essential fatty acids, calcium, magnesium, B-complex vitamins, lecithin, taurine and chamomile.

Pain Reducers

Non-limiting examples include: lavender, rosemary, capsaicin, peppermint, *eucalyptus*, ginger, feverfew, and turmeric Sleep Agents Non-limiting examples of natural or botanical ingredients that are marketed as a way to improve sleep include: chamomile, lavender, lemon balm and melatonin.

Stress Agents

Non-limiting examples of ingredients that are marketed toward management of stress include: ashwagandha, L-theanine, B-complex vitamins, *Rhodiola rosea*, melatonin, glycine, and kava.

Prebiotics

Prebiotics have been defined as nondigestible food ingredients that beneficially affect the host by selectively stimulating the growth and/or activity of one or a limited number of bacteria in the colon.

Non-limiting examples of prebiotics include: inulin, fructooligosaccharides (FOS), and galactooligosaccharides (GOS) and combinations thereof.

Probiotics

Probiotics are live microorganisms that are intended to have health benefits when consumed or applied to the body. They can be found in yogurt and other fermented foods, dietary supplements, and beauty products.

Probiotics may contain a variety of microorganisms. The most common are bacteria that belong to groups called *Lactobacillus* and *Bifidobacterium*. Other bacteria may also be used as probiotics, and so may yeasts such as *Saccharomyces boulardii*.

Different types of probiotics may have different effects. For example, if a specific kind of *Lactobacillus* helps prevent an illness, that doesn't necessarily mean that another kind of *Lactobacillus* or any of the *Bifidobacterium* probiotics would do the same thing.

There are a plethora of probiotics marketed for a variety of health benefits. Non-limiting examples of marketed probiotics include: *Bifidobacterium breve, Bifidobacterim longum* 35624, *Bifidobacterium lactis, Lactobacillus rhamnosus, Lactobacillus reuteri, Lactobacilus gasseri, Saccharomyces boulardii, Saccharomyces cerevisiae* or combinations thereof.

Rheological Solid Oral Composition Properties

Stability Temperature

Stability temperature, as used herein, is the temperature at which most or all of the crystallizing agent completely dissolves into an aqueous phase, such that a composition no longer exhibits a stable solid structure and may be considered a liquid. In embodiments of the present invention the stability temperature range may be from about 40° C. to about 95° C., about 40° C. to about 90° C., about 50° C. to about 80° C., or from about 60° C. to about 70° C., as these temperatures are typical in a supply chain. Stability temperature can be determined using the THERMAL STABILITY TEST METHOD, as described below.

Firmness

Depending on the intended application firmness of the composition may also be considered. The firmness of a composition may, for example, be expressed in Newtons of force. For example, compositions of the present invention comprising 1-3 wt % crystallizing agent may give values of about 4-about 12 N, in the form of a pill. As is evident, the firmness of the composition according to embodiments of the present invention may, for example, be such that the composition is advantageously self-supporting and can release liquids and/or actives upon application of low to moderate force, for example upon contact with a surface The composition of the invention may also be transparent or clear, including for example, a composition without pigments. Preferred firmness is between about 0.1 N to about 50.0 N, more preferably between about 0.5 N to about 40.0 N, more preferably between about 1.0 N to about 30.0 N and most preferably between about 2.5 N to about 15.0 N. The firmness may be measured using the FIRMNESS TEST METHOD, as described below.

Aqueous Phase Expression

Depending on the intended application, such as a chewing form of a rheological solid oral composition aqueous phase expression of the composition may also be considered. This is a measure of the amount of work need per unit volume to express the aqueous phase from the compositions, with larger values meaning it becomes more difficult to express liquid. A low value might be preferred, for example, when applying the composition to the skin. A high value might be preferred, for example, when the composition is applied to a substrate that requires dry-to-the-touch-but-wet-to-the-wipe' properties. Preferred values are between about 100 J m-3 to about 8,000 J m-3, more preferably between about 1,000 J m-3 to about 7,000 J m-3, and most preferably between about 2,000 J m-3 to about 5,000 J m-3. The liquid expression may be measured using the AQUEOUS PHASE EXPRESSION TEST METHOD, as described herein.

Firmness Test Method

All samples and procedures are maintained at room temperature (25±3° C.) prior to and during testing, with care to ensure little or no water loss.

All measurements were made with a TA-XT2 Texture Analyzer (Texture Technology Corporation, Scarsdale, N.Y., U.S.A.) outfitted with a standard 45° angle penetration cone tool (Texture Technology Corp., as part number TA-15).

To operate the TA-XT2 Texture Analyzer, the tool is attached to the probe carrier arm and cleaned with a low-lint wipe. The sample is positioned and held firmly such that the tool will contact a representative region of the sample. The tool is reset to be about 1 cm above the product sample.

The sample is re-position so that the tool will contact a second representative region of the sample. A run is done by moving the tool at a rate of 2 mm/second exactly 10 mm into the sample. The "RUN" button on the Texture Analyzer can be pressed to perform the measurement. A second run is done with the same procedure at another representative region of the sample at sufficient distance from previous measurements that they do not affect the second run. A third run is done with the same procedure at another representative region of the sample at sufficient distance from previous measurements that they do not affect the third run.

The results of the FIRMNESS TEST METHOD, are all entered in the examples in the row entitles 'Firmness'. In general, the numeric value is returned as the average of the maximum value of three measurements as described above, except in one of the two cases:
1) the composition does not form a homogenous rheological solid (e.g. completely or partially liquid), the value of 'NM1' is returned;
2) and, the composition curds during making, the value of 'NM2' is returned.

Thermal Stability Test Method

All samples and procedures are maintained at room temperature (25±3° C.) prior to testing.

Sampling is done at a representative region on the sample, in two steps. First, a spatula is cleaned with a laboratory wipe and a small amount of the sample is removed and discarded from the top of the sample at the region, to create a small square hole about 5 mm deep. Second, the spatula is cleaned again with a clean laboratory wipe, and a small amount of sample is collected from the square hole and loaded into DSC pan.

The sample is loaded into a DSC pan. All measurements are done in a high-volume-stainless-steel pan set (TA part #900825.902). The pan, lid and gasket are weighed and tared on a Mettler Toledo MT5 analytical microbalance (or equivalent; Mettler Toledo, LLC., Columbus, OH). The sample is loaded into the pan with a target weight of 20 mg (+/−10 mg) in accordance with manufacturer's specifications, taking care to ensure that the sample is in contact with the bottom of the pan. The pan is then sealed with a TA High Volume Die Set (TA part #901608.905). The final assembly is measured to obtain the sample weight.

The sample is loaded into TA Q Series DSC (TA Instruments, New Castle, DE) in accordance with the manufacture instructions. The DSC procedure uses the following settings: 1) equilibrate at 25° C.; 2) mark end of cycle 1; 3) ramp 1.00° C./min to 90.00° C.; 4) mark end of cycle 3; then 5) end of method; Hit run.

The results of the TEMPERATURE STABILITY TEST METHOD, are all entered in the examples in the row entitles 'Temperature'. In general, the numeric value is returned as described above, except in one of the two cases:
1) the composition does not form a homogenous rheological solid (e.g. completely or partially liquid) and is not suitable for the measurement, the value of 'NM3' is returned;
2) and, the composition curds during making and is not suitable for the measurement, the value of 'NM4' is returned.

Aqueous Phase Expression Test Method

All samples and procedures are maintained at room temperature 25 (±3° C.) prior to testing.

Measurements for the determination of aqueous phase expression were made with a TA Discovery HR-2 Hybrid Rheometer (TA Instruments, New Castle, DE) and accompanying TRIOS software version 3.2.0.3877, or equivalent. The instrument is outfitted with a DHR Immobilization Cell (TA Instrument) and 50 mm flat steel plate (TA Instruments). The calibration is done in accordance with manufacturer's recommendations, with special attention to measuring the bottom of the DHR Immobilization Cell, to ensure this is established as gap=0.

Samples are prepared in accordance with EXAMPLE procedures. It is critical that the sample be prepared in Speed Mixer containers (Flak-Tech, Max 60 Cup Translucent, Cat #501 222t), so that the diameter of the sample matches the diameter of the HR-2 Immobilization Cell. The sample is released from the containers by running a thin spatula between the edge of the container and the sample. The container is gently turned over and placed on a flat surface. A gentle force is applied to the center of the bottom of the overturned container, until the sample releases and gently glides out of the container. The sample is carefully placed in the center ring of the DHR Immobilization Cell. Care is used to ensure that the sample is not deformed and re-shaped through this entire process. The diameter of the sample should be slightly smaller than the inner diameter of the ring. This ensures that force applied to the sample in latter steps does not significantly deform the cylindrical shape of the sample, instead allowing the aqueous phase to escape through the bottom of the sample. This also ensures that any change in the height of the sample for the experiment is equivalent to the amount of aqueous phase expressed during the test. At the end of the measurement, one should confirm that the aqueous phase is indeed expressed from the sample through the measurement, by looking for aqueous phase in the effluent tube connected to the Immobilization Cell. If no aqueous phase is observed, the sample is deemed not to express aqueous phase and is not inventive.

Set the instrument settings as follows. Select Axial Test Geometry. Then, set "Geometry" options: Diameter=50 mm; Gap=45000 um; Loading Gap=45000 um; Trim Gap Offset=50 um; Material='Steel'; Environmental System="Peltier Plate". Set "Procedure" options: Temperature=25° C.; Soak Time=0 sec; Duration=2000 sec; Motor Direction="Compression"; Constant Linear Rate=2 um sec-1; Maximum Gap Change=0 um; Torque=0 uN·m; Data Acquisition='save image' every 5 sec.

Manually move the steel tool within about 1000 um of the surface of the sample, taking care that the tool does not touch the surface. In the "Geometry" options, reset Gap to this distance.

Start the run.

The data is expressed in two plots:
1) Plot 1: Axial Force (N) on the left-y-axis and Step Time (s) on the x-axis;
2) Plot 2: Gap (um) on the right-y-axis and Step Time (s) on the x-axis.

The Contact Time—T(contact), is obtained from Plot 1. The T(contact) is defined as the time when the tool touches the top of the sample. The T(contact) is the Step Time when the first Axial Force data point exceeds 0.05 N.

The Sample Thickness—L, is the gap distance at the Contact Time, and expressed in units of meters.

The Time of Compression—T(compression), is the Step Time at which the gap is 0.85*L, or 15% of the sample.

The Work required to squeeze the aqueous phase from the structure is the area under the Axial Force curve in Plot 1 between T(contact) and T(compression) multiplied by Constant Linear Rate, or 2e-6 m s-1 normalized by dividing the total volume of expressed fluids, and is expressed in units of Joules per cubic meter (J m-3).

The results of the AQUEOUS PHASE EXPRESSION TEST METHOD, are all entered in the examples in the row entitled 'AP Expression'. In general, the numeric value, as the average of at least two values is returned as described, except in one of the three cases:
1) the composition does not form a homogenous rheological solid (e.g. completely or partially liquid) and is not suitable for the measurement, the value of 'NM5' is returned;
2) the composition curds during making and is not suitable for the measurement, the value of 'NM6' is returned;
3) the composition is a rheological solid but too soft to effectively load in the device, the value of 'NM7' is returned;
4) and the composition is too hard so that the force exceeds 50 N before the 15% compression, the value of 'NM8' is returned;

Blend Test Method

All samples and procedures are maintained at room temperature 25 (±3° C.) prior to testing.

Samples are prepared by weighing 4 mg (+/−1 mg) of a 3% fatty acid in water solution into a scintillation vial with a PTFE septum and then adding 2 mL of ethanol ACS grade or equivalent. A cap is then placed on the vial and the sample is mixed until the sample is homogenous. The vial is then placed in a 70° C. oven with the cap removed to evaporate the ethanol (and water), after which it is allowed to cool to room temperature.

A pipettor is used to dispense 2 mL of BF3-methanol (10% Boron Trifluoride in methanol, Sigma Aldrich #15716) into the vial, and the capped tightly. The sample is placed on a VWR hot plate set at 70° C. until the sample is homogenous, and then for an additional 5 min before cooling to room temperature.

A saturated sodium chloride solution is prepared by adding sodium chloride salt ACS grade or equivalent to 10 mL of distilled water at ambient temperature. Once the vial is at room temperature, 4 mL of the saturated sodium chloride solution are added to the vial and swirled to mix. Then, 4 mL of hexane, ACS grade or equivalent, are added to the vial which is then capped and shaken vigorously. The sample is then placed on a stationary lab bench and until the hexane and water separate into two phases.

A transfer pipet is used to transfer the hexane layer into a new 8 mL vial, and then 0.5 g of sodium sulfate, ACS grade or equivalent, is added to dry the hexane layer. The dried hexane layer is then transferred to a 1.8 mL GC vial for analysis.

Samples are analyzed using an Agilent 7890B (Agilent Technologies Inc., Santa Carla, CA), or equivalent gas chromatograph, equipped with capillary inlet system and flame ionization detector with peak integration capabilities, and an Agilent DB-FastFAME (#G3903-63011), or equivalent column.

The gas chromatograph conditions and settings are defined as follows: uses Helium UHP grade, or regular grade helium purified through gas purification system, as a carrier gas, and is set at a constant flow mode of 1.2 mL/minute (velocity of 31.8 cm/sec); has an oven temperature program that is set for 100° C. for 2 minutes, and increased at a rate of 10° C. per minute until it reaches 250 C for 3 minutes; the injector temperature is set to 250° C. and the detector temperature is set to 280° C.; the gas flows are set to 40 mL/minute for hydrogen, 400 mL/minute for air, and 25 mL/minute for the Make-up (helium); and the injection volume and split ratio is defined a 1 uL, split 1:100 injection.

The instrument is calibrated using a 37-Component FAME standard mixture (Supelco #CRM47885), or equivalent calibration standard. The Response Factor and Normalized Response Factor based on n-C16 FAME standard.

Response Factor is calculated for each component by dividing the FAME FID Area account of an analyte in the calibration solution by the concentration of the identical FAME analyte in the calibration solution.

The Normalized Response Factor is calculated by dividing the Response Factor of each component by the Response Factor of n-C16 methyl ester that has been defined as 1.00.

The Normalized FAME FID Area is calculated with the Normalized Response Factor by dividing the FAME FID area (component) by the Normalized Response Factor (component).

The FAME weight percent of each component is calculated by dividing the Normalized FAME FID area (component) by the Normalized FAME FID area (total of each component) and then multiplying by one hundred.

The Conversion Factor from FAME to free Fatty Acid is calculated by dividing the Molecular Weight of the Target Fatty Acid by the Molecular Weight of the Target FAME.

The Normalized Fatty Acid FID Area is calculated by multiplying the Normalized FAME FID Area by the Conversion Factor from FAME to free Fatty Acid.

The Fatty Acid Weight Percent of each component is calculated by dividing the Normalized Fatty Acid FID Area (component) by the Normalized FA FID Area (total of each component) and the multiplying the result by one hundred.

The Conversion Factor from FAME to free Fatty Acid Sodium Salt is calculated by dividing the Molecular Weight of the Target Fatty Acid Sodium Salt by the molecular weight of the Target FAME.

The Normalized Fatty Acid Sodium Salt FID Area is calculated by multiplying the Normalized FAME FID Area by the Conversion Factor from FAME to free Fatty Acid Sodium Salt.

The Weight percent of each Fatty Acid Sodium Salt component was calculated by dividing the normalized Fatty Acid Sodium Salt FID area (component) by the Normalized Fatty Acid Sodium Salt FID area (total of each component) and then multiplying by one hundred.

Purity of the crystallizing agent is described in the following ways:

Optimal Purity—Po, which is the mass fraction of the optimal chain length molecules in the crystallizing agent blend calculated as:

$$P_o = \frac{\Sigma M_o}{M_t}$$

where Mo is the mass of each optimal chain length in the crystallizing agent and Mt is the total mass of the crystallizing agent.

Single Purity—Ps, which is the mass fraction of the most common chain length in the crystallizing agent blend calculated as:

$$P_s = \frac{M_s}{M_t}$$

where Ms is the mass of the most common chain length in the crystallizing agent and Mt is the total mass of the crystallizing agent. The value is expressed in brackets—[Ms], if the most common chain length is selected from the group of unsuitable chain length molecules.

EXAMPLES

Materials List
  (1) Water: Millipore, Burlington, MA (18 m-ohm resistance)
  (2) Sodium myristate (sodium tetradecanoate, NaC14): TCI Chemicals, Cat. #M0483
  (3) Sodium palmitate (sodium hexadecanoate, NaC16): TCI Chemicals, Cat. #P0007
  (4) Sodium stearate (sodium octadecanoate, NaC18): TCI Chemicals, Cat. #S0081
  (5) Acetaminophen (P&G, lot 1950041)
  (6) Diphenhydramine (P&G, lot 78081)
  (7) Dextromethorphan Hbr (a supplier)
  (8) Doxylamine Succinate (a supplier)
  (9) Phenylephrine HCl (a supplier)

(10) Sugar (Domino, UPC: 0004920004350)
(11) Vanilla (Kroger, #01110080622)

Example 1

Samples NUMBERS/NAMES show different compositions of a pill compositions. In one embodiment, the composition immobilizes the actives creating a pill of the lubricous formulation. In another embodiment, the composition coats a solid pill composition, presenting a lubricious layer allowing the solid pill to be more easily swallowed.

Preparation of Composition

A unit dose of oral medication is prepared based on a rheological solid. Rheological solid oral compositions are be formulated as described above. To the heated water, the following ingredients are added:

Step 1. 1000 grams of water is added to a 2 liter reaction vessel. Crystallizing agent is added to the reaction vessel. The vessel is fitted with an overhead stirrer assembly, which is activated to create a modest vortex in the mixture. The mixture is heated to 80° C. until the all the crystallizing agent has completely dissolved, as event by a completely clear solution.

Step 2. The mixture is cooled to about 40° C. over the course of no more than 5 minutes. In one embodiment, the mixture is poured into a pill mold. The compositions may then be placed in 4° C. room, to form the rheological solid oral composition as soon as possible. In other embodiment, a traditional solid pill may be coated with a rheological solid oral composition on the outside to make it easier to swallow.

TABLE 1

| | Sample A Inventive | Sample B Inventive | Sample C Inventive | Sample D Inventive |
|---|---|---|---|---|
| (1) water | 96.8% | 97.0% | 97.0 g | 96.1 g |
| (2) Sodium Myristate (NaC14) | — | — | — | 2.9 g |
| (3) Sodium Palmitate (NaC16) | 2.9% | 2.9% | 2.9 g | — |
| (4) Sodium Stearate (NaC18) | — | — | — | 0.9% |
| (5) Acetaminophen | 0.3% | — | — | — |
| (7) Dextromethorphan Hbr | — | 0.1% | — | — |
| (8) Doxylamine Succinate | — | — | 0.1% | — |
| (9) Phenylephrine HCl | — | — | — | 0.1% |
| Form | Pass | Pass | Pass | Pass |
| % Crystallizing Agent | 2.9% | 2.9% | 2.9% | 3.8% |
| % Active | 0.3% | 0.1% | 0.1% | 0.1% |

Example 2

Figure 3:
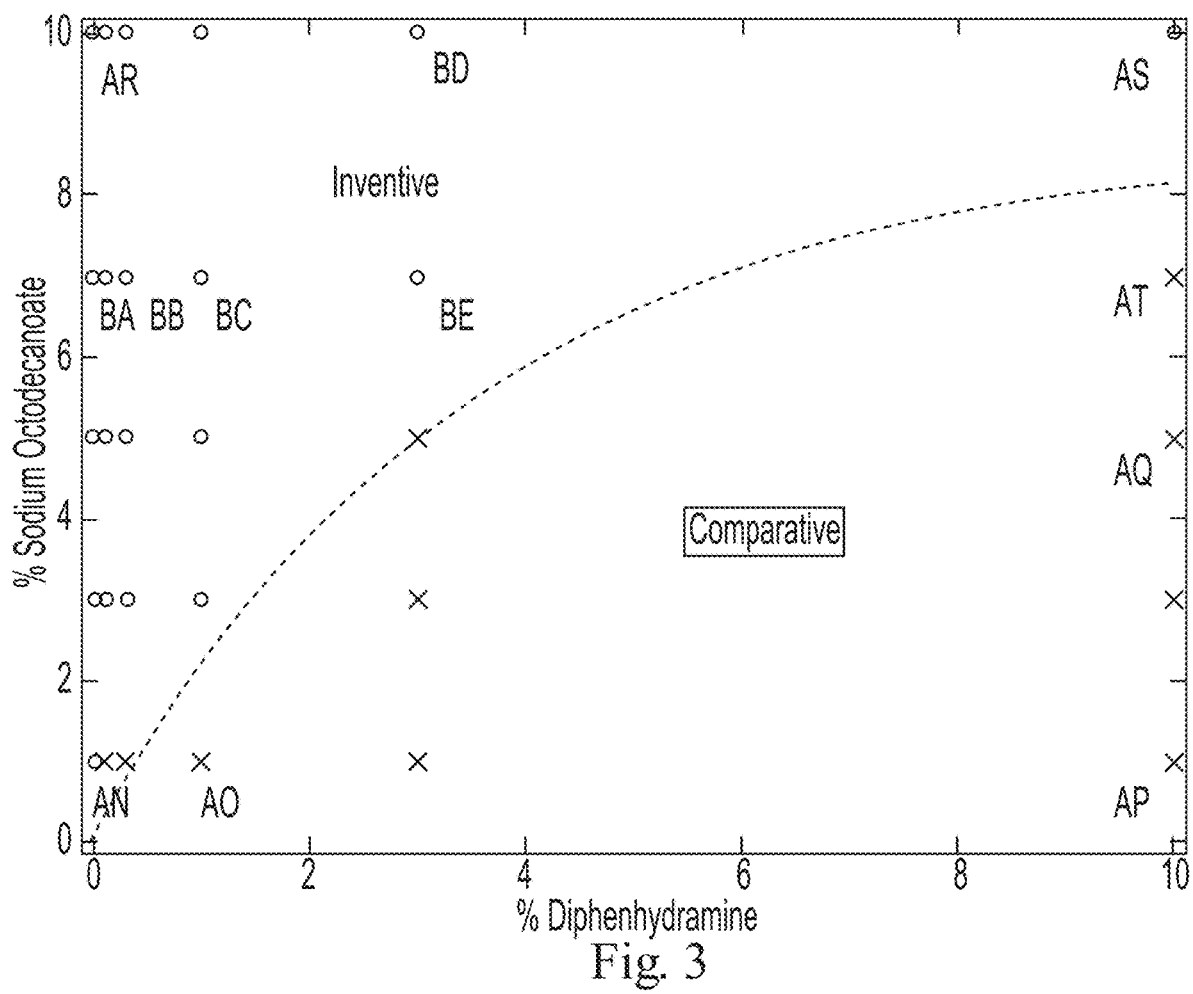

Shows inventive and comparative compositions containing crystallizing agent and acetaminophen specifically:
Sample E-Sample K—prepared with sodium hexadecanoate crystallizing agent and acetaminophen;
Sample L-Sample R—prepared with sodium tetradecanoate crystallizing agent and acetaminophen;
Sample S-Sample Y—prepared with sodium octadecanoate crystallizing agent and acetaminophen, with some points shown in FIG. 3;

All the compositions show the same basic trends. With no added acetaminophen, all the compositions are solid compositions, as previously described. With increasing amounts of acetaminophen, more crystallizing agent is required. These trends are captured in FIG. 3. Each point on the plot represents a single preparation, although not all weights used to prepare these compositions are in TABLE 6-TABLE 9; compositions shown in the Tables have an example number to the lower right of the point on the plot. Inventive compositions result in 'solid' and are marked by an open circle; comparative compositions result in 'liquids' or liquid-solid mixtures' and are market by dark crosses. We envision a line that separates the inventive compositions across the figure, where compositions above the line are inventive compositions and compositions below the line are comparative compositions. The same exercise can be done with sodium hexadecanoate (including Sample E-Sample K) and with sodium tetradecanoate (including Sample L-Sample R).

Preferred compositions include those with the concentration of crystallizing agents <10 wt % and more preferred composition include those with the concentration of crystallizing agents <8 wt %. With concentration of the crystallizing agent in significant excess of the inventive-comparative composition line, the preparations can become too hard to express what an exhibit the lubrication properties. Preferred compositions are less than 5% crystallization above this line for any particular concentration of acetaminophen; more preferred compositions are less than 3% crystallization above this line for any particular concentration of acetaminophen; most referred compositions are less than 1% crystallization above this line for any particular concentration of acetaminophen. Sample Z-Sample AB (FIG. 3) show that increasing acetaminophen with a constant crystallizing agent composition softens the resulting composition. Sample AC-Sample AE (FIG. 3) show that decreasing the amount of crystallizing agent at a constant acetaminophen concentration also softens the resulting composition leading to enhanced water expression. In fact, it is very difficult to express water from composition Sample AC (NM8) while it is much easier to express water from composition Sample AE (4,603 J m-3). By adjusting both variables, one arrives at an optimal set of compositions for pill lubricity.

Preparation of Composition

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 125 ml stainless steel beaker (Thermo Fischer Scientific, Waltham, MA).

Solutions were prepared by adding water (1), a surfactant (2-4), and an oral active agent (5) to the beaker. The beaker was placed on the heated mixing device. The overhead stirrer was placed in the beaker and set to rotate at 225 rpm. The heater was set, and the preparation was heated to 80° C. The solution was then placed in 20 mL vials (DWK, Millville, NJ, Vials with Unattached Caps, cat. No. 56941-513).

The compositions were allowed cool to room temperature and allowed to sit quiescently for 24 hours. The composition is assigned a value of Form='pass', if the composition is both solid and homogeneous, and the composition represents a viable pill composition; The composition is assigned a value of Form='fail', if the composition is both liquid or a mixture of solid and liquid, and the composition does not represent a viable pill composition Solution was allowed to cool and resulting form was recorded. Form='pass', is given to a composition that is a homogeneous solid; Form='fail', is given to a composition that is either liquid or some fraction of (liquid+solid).

TABLE 2

|  | Sample E Inventive | Sample F Comparative | Sample G Comparative | Sample H Inventive |
| --- | --- | --- | --- | --- |
| (1) Water | 24.7422 g | 24.5144 g | 22.5187 g | 21.2938 g |
| (2) NaC14 | — | — | — | — |
| (3) NaC16 | 0.2509 g | 0.2493 g | 0.2517 g | 1.2506 g |
| (4) NaC18 | — | — | — | — |
| (5) Acetaminophen | 0.0308 g | 0.2559 g | 2.4982 g | 2.5088 g |
| Form | pass | fail | fail | pass |
| % Crystallizing Agent | 1.00% | 1.00% | 1.00% | 4.99% |
| % Active | 0.03% | 1.02% | 9.89% | 10.01% |

TABLE 3

|  | Sample I Inventive | Sample J Inventive | Sample K Inventive |
| --- | --- | --- | --- |
| (1) Water | 20.7542 g | 22.4905 g | 20.0035 g |
| (2) NaC14 | — | — | — |
| (3) NaC16 | 1.7549 g | 2.5022 g | 2.4983 g |
| (4) NaC18 | — | — | — |
| (5) Acetaminophen | 2.4992 g | 0.0289 g | 2.4983 g |
| Form | pass | pass | pass |
| % Crystallizing Agent | 7.02% | 10.00% | 10.00% |
| % Active | 9.99% | 0.12% | 10.00% |

TABLE 4

|  | Sample L Inventive | Sample M Comparative | Sample N Comparative | Sample O Inventive |
| --- | --- | --- | --- | --- |
| (1) Water | 24.729 g | 24.5067 g | 22.2691 g | 21.2124 g |
| (2) NaC14 | 0.2494 g | 0.2499 g | 0.2505 g | 1.2508 g |
| (3) NaC16 | — | — | — | — |
| (4) NaC18 | — | — | — | — |
| (5) Acetaminophen | 0.0265 g | 0.2509 g | 2.5085 g | 2.5063 g |
| Form | pass | fail | fail | pass |
| % Crystallizing Agent | 1.00% | 1.00% | 1.00% | 5.01% |
| % Active | 0.11% | 1.00% | 10.02% | 10.04% |

TABLE 5

|  | Sample P Inventive | Sample Q Inventive | Sample R Inventive |
| --- | --- | --- | --- |
| (1) Water | 20.7251 g | 22.4604 g | 20.0197 g |
| (2) NaC14 | 1.7491 g | 2.5009 g | 2.4999 g |
| (3) NaC16 | — | — | — |
| (4) NaC18 | — | — | — |
| (5) Acetaminophen | 2.5073 g | 0.0255 g | 2.4918 g |
| Form | pass | pass | pass |
| % Crystallizing Agent | 7.00% | 10.01% | 10.00% |
| % Active | 10.04% | 0.10% | 9.96% |

TABLE 6

|  | Sample S Inventive | Sample T Comparative | Sample U Comparative | Sample V Inventive |
|---|---|---|---|---|
| (1) Water | 24.7551 g | 24.4993 g | 22.2721 g | 21.2741 g |
| (2) NaC14 | — | — | — | — |
| (3) NaC16 | — | — | — | — |
| (4) NaC18 | 0.2454 g | 0.2493 g | 0.2517 g | 1.2571 g |
| (5) Acetaminophen | 0.02584 g | 0.2501 g | 2.5016 g | 2.5061 g |
| Form | pass | fail | fail | pass |
| % Crystallizing Agent | 0.98% | 1.00% | 1.01% | 5.02% |
| % Active | 0.10% | 1.00% | 10.00% | 10.01% |

TABLE 7

|  | Sample W Inventive | Sample X Inventive | Sample Y Inventive |
|---|---|---|---|
| (1) Water | 20.7082 g | 22.4776 g | 20.0063 g |
| (2) NaC14 | — | — | — |
| (3) NaC16 | — | — | — |
| (4) NaC18 | 1.7559 g | 2.5105 g | 2.49740 g |
| (5) Acetaminophen | 2.5124 g | 0.0268 g | 2.5116 g |
| Form | pass | pass | pass |
| % Crystallizing Agent | 7.03% | 10.02% | 9.98% |
| % Active | 10.06% | 0.11% | 10.04% |

TABLE 8

|  | Example Z Inventive | Example AA Inventive | Example AB Inventive |
|---|---|---|---|
| (1) Water | 48.4144 g | 48.3379 g | 48.0055 g |
| (2) NaC14 | — | — | — |
| (3) NaC16 | — | — | — |
| (4) NaC18 | 1.5059 g | 1.4999 g | 1.5036 g |
| (5) Acetaminophen | 0.0498 g | 0.1503 g | 0.5030 g |
| Form | pass | pass | pass |
| % Crystallizing Agent | 3.0% | 3.0% | 3.0% |
| % Active | 0.1% | 0.3% | 1.0% |
| Firmness | 1.41N | 1.03N | 0.65N |

TABLE 9

|  | Example AC Inventive | Example AD Inventive | Example AE Inventive |
|---|---|---|---|
| (1) Water | 43.4972 g | 45.0247 g | 45.9985 g |
| (2) NaC14 | — | — | — |
| (3) NaC16 | — | — | — |
| (4) NaC18 | 5.0018 g | 3.4992 g | 2.4963 g |
| (5) Acetaminophen | 1.5002 g | 1.5079 g | 1.5002 g |
| Form | pass | pass | pass |
| % Crystallizing Agent | 10.0% | 7.0% | 5.0% |
| % Active | 3.0% | 3.0% | 3.0% |
| Firmness | 5.61N | 2.68N | 1.35N |
| Water Expression | NM8 | — | 4,603 J m-3 |

Example 3

Figure 4:
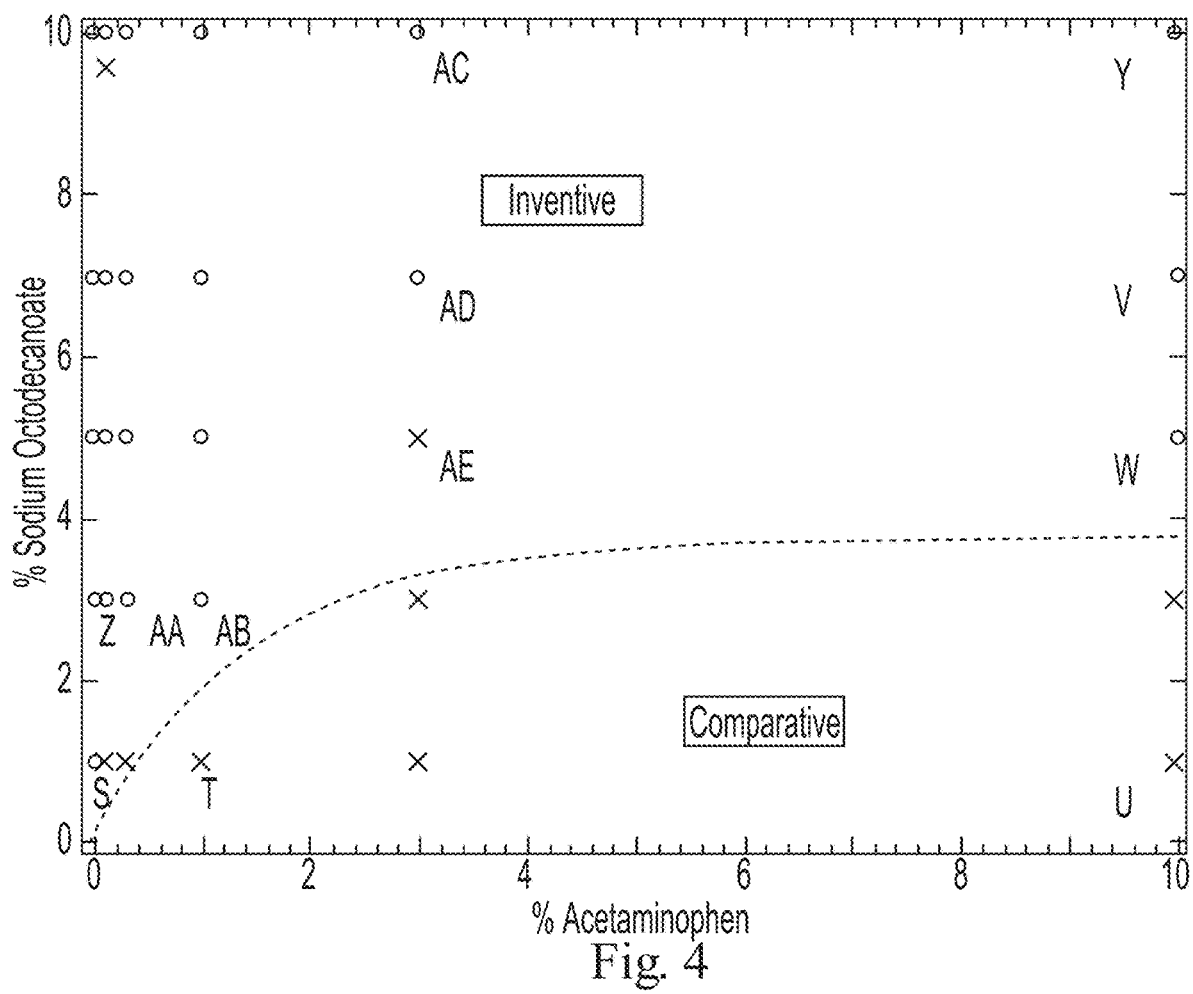

Shows inventive and comparative compositions containing crystallizing agent and dephenhydramine specifically:
Sample AF-Sample AL—prepared with sodium hexadecanoate crystallizing agent and acetaminophen;
Sample AM-Sample AS—prepared with sodium tetadecanoate crystallizing agent and acetaminophen;
Sample AT-Sample AZ—prepared with sodium octadecanoate crystallizing agent and acetaminophen, with some points shown in FIG. 4;

All the compositions show the same basic trends. With no added diphenhydramine, all the compositions are viable solid compositions, as previously described. With increasing amounts of diphenhydramine, more crystallizing agent is required. These trends are captured in a FIG. 4, Each point on the plot represents a single preparation, although not all weights used to prepare these compositions are in TABLE 14-TABLE 17; compositions shown in the Tables have an example number to the lower right of the point on the plot. Inventive compositions result in 'solid' and are marked by an open circle; comparative compositions result in 'liquids' or 'liquid-solid mixtures' and are market by dark crosses. We envision a line that separates the inventive compositions across the figure, where compositions above the line are inventive compositions and compositions below the line are comparative compositions. The same exercise can be done with sodium hexadecanoate (including Sample Z-Sample AF) and with sodium tetradecanoate (including Sample AG-Sample AM).

Preferred compositions include those with the concentration of crystallizing agents <10 wt % and more preferred composition include those with the concentration of crystallizing agents <8 wt %. With concentration of the crystallizing agent in significant excess of the inventive-comparative composition line, the preparations can become too hard to express what an exhibit the lubrication properties. Preferred compositions are less than 5% crystallization above this line for any particular concentration of acetaminophen; more referred compositions are less than 3% crystallization above this line for any particular concentration of acetaminophen; most referred compositions are less than 1% crystallization above this line for any particular concentration of acetaminophen. Sample BA-Sample BE (FIG. 4) show that increasing diphenhydramine with a constant crystallizing agent composition softens the resulting composition. Sample BD-Sample BE (FIG. 4) show that decreasing the amount of crystallizing agent at a constant diphenhydramine concentration also softens the resulting composition leading to enhanced water expression. In fact, it is comparatively difficult to express water from composition Sample BD (2,630 J m-3) while it is much easier to express water from composition Sample BE (413 J m-3). In this case—in contrast to Sample AC and Sample AE, the higher concentration of crystallizing may be preferred due to the softness of Sample BE. By adjusting both variables, one arrives at an optimal set of compositions for pill lubricity within the claim limits.

In combination with Example 2, this example also demonstrates the active matters. While the trends are similar between acetaminophen and dephenhydramine, the crystallizing agent must be adjusted between different actives. For example, Sample Y is inventive with acetaminophen but Sample AZ is comparative with dephenhydramine.

Preparation of Composition

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 125 ml stainless steel beaker (Thermo Fischer Scientific, Waltham, MA).

Solutions were prepared by adding water (1), a surfactant (2-4), and an oral active agent (5, 6) to the beaker. The beaker was placed on the heated mixing device. The overhead stirrer was placed in the beaker and set to rotate at 225 rpm. The heater was set, and the preparation was heated to 80° C. The solution was then placed in 20 mL vials (DWK, Millville, NJ, Vials with Unattached Caps, cat. No. 56941-513).

Solution was allowed to cool and resulting form was recorded. Form='pass', is given to a composition that is a homogeneous solid; Form='fail', is given to a composition that is either liquid or some fraction of (liquid+solid).

TABLE 10

|  | Sample AF Inventive | Sample AG Comparative | Sample AH Comparative | Sample AI Comparative |
| --- | --- | --- | --- | --- |
| (1) Water | 24.7478 g | 24.5104 g | 22.2571 g | 21.2615 g |
| (2) NaC14 | — | — | — | — |
| (3) NaC16 | 0.2524 g | 0.2504 g | 0.2502 g | 1.2479 g |
| (4) NaC18 | — | — | — | — |
| (6) Diphenhydramine | 0.0283 g | 0.2525 g | 2.5056 g | 2.4955 g |
| Form | pass | fail | fail | fail |
| % Crystallizing Agent | 1.01% | 1.00% | 1.00% | 4.99% |
| % Active | 0.11% | 1.01% | 10.02% | 9.98% |

TABLE 11

|  | Sample AJ Inventive | Sample AK Inventive | Sample AL Comparative |
| --- | --- | --- | --- |
| (1) Water | 20.7681 g | 22.4720 g | 20.0472 g |
| (2) NaC14 | — | — | — |
| (3) NaC16 | 1.7497 g | 2.4985 g | 2.5019 g |
| (4) NaC18 | — | — | — |
| (6) Diphenhydramine | 2.5046 g | 0.0266 g | 2.4192 g |
| Form | pass | pass | fail |
| % Crystallizing Agent | 6.99% | 10.00% | 10.02% |
| % Active | 10.01% | 0.11% | 9.69% |

TABLE 12

|  | Sample AM Inventive | Sample AN Comparative | Sample AO Comparative | Sample AP Comparative |
| --- | --- | --- | --- | --- |
| (1) Water | 24.7565 g | 24.5137 g | 22.2153 g | 21.2627 g |
| (2) NaC14 | 0.2502 g | 0.2490 g | 0.2498 g | 1.2501 g |
| (3) NaC16 | — | — | — | — |
| (4) NaC18 | — | — | — | — |
| (6) Diphenhydramine | 0.0247 g | 0.2507 g | 2.5997 g | 2.5060 g |
| Form | pass | fail | fail | fail |
| % Crystallizing Agent | 1.01% | 1.00% | 1.00% | 5.00% |
| % Active | 0.10% | 1.00% | 10.37% | 10.02% |

TABLE 13

|  | Sample AQ Inventive | Sample AR Inventive | Sample AS Comparative |
|---|---|---|---|
| (1) Water | 20.7163 g | 22.4858 g | 20.0168 g |
| (2) NaC14 | 1.7504 g | 2.4968 g | 2.4963 g |
| (3) NaC16 | — | — | — |
| (4) NaC18 | — | — | — |
| (6) Diphenhydramine | 2.5025 g | 0.0264 g | 2.5035 g |
| Form | pass | pass | fail |
| % Crystallizing Agent | 7.01% | 9.98% | 9.98% |
| % Active | 10.02% | 0.11% | 10.01% |

TABLE 14

|  | Sample AT Inventive | Sample AU Comparative | Sample AV Comparative | Sample AW Comparative |
|---|---|---|---|---|
| (1) Water | 24.7211 g | 24.5025 g | 22.2153 g | 21.2627 g |
| (2) NaC14 | — | — | — | — |
| (3) NaC16 | — | — | — | — |
| (4) NaC18 | 0.2501 g | 0.2517 g | 0.2508 g | 1.2564 g |
| (6) Diphenhydramine | 0.0270 g | 0.2517 g | 2.4987 g | 2.4895 g |
| Form | pass | fail | fail | fail |
| % Crystallizing Agent | 1.00% | 1.01% | 1.00% | 5.02% |
| % Active | 0.11% | 1.01% | 10.01% | 9.95% |

TABLE 15

|  | Sample AX Inventive | Sample AY Inventive | Sample AZ Comparative |
|---|---|---|---|
| (1) Water | 20.6790 g | 22.4858 g | 20.0168 g |
| (2) NaC14 | — | — | — |
| (3) NaC16 | — | — | — |
| (4) NaC18 | 1.7525 g | 2.5024 g | 2.5009 g |
| (6) Diphenhydramine | 2.4988 g | 0.0295 g | 2.5004 g |
| Form | pass | pass | fail |
| % Crystallizing Agent | 7.03% | 10.00% | 10.00% |
| % Active | 10.02% | 0.12% | 9.99% |

TABLE 16

|  | Sample BA Inventive | Sample BB Inventive | Sample BC Inventive |
|---|---|---|---|
| (1) Water | 46.4843 g | 46.3252 g | 46.040 g |
| (2) NaC14 | — | — | — |
| (3) NaC16 | — | — | — |
| (4) NaC18 | 3.5066 g | 3.5124 g | 3.5042 g |
| (6) Diphenhydramine | 0.0507 g | 0.1500 g | 0.5065 g |
| Form | pass | pass | pass |
| % Crystallizing Agent | 7.0% | 7.0% | 7.0% |
| % Active | 0.1% | 0.3% | 1.0% |
| Firmness | 5.01N | 4.80N | 4.26N |

TABLE 17

|  | Sample BD Inventive | Sample BE Inventive |
|---|---|---|
| (1) Water | 43.4982 g | 45.0663 g |
| (2) NaC14 | — | — |
| (3) NaC16 | — | — |
| (4) NaC18 | 5.0109 g | 3.5019 g |
| (6) Diphenhydramine | 1.5077 g | 1.4973 g |
| Form | pass | pass |
| % Crystallizing Agent | 10.0% | 7.0% |
| % Active | 3.0% | 3.0% |
| Firmness | 2.55N | 0.89N |
| Water Expression | 2,630 J m-3 | 413 J m-3 |

Example 4

Non-limiting examples, for the inclusion of flavors into compositions, to make the pills more agreeable to the consumers. Sample BF-Sample BI (TABLE 18) demonstrate that different crystallizing agents can be used to incorporate at least 10 wt % table sugar, to enhance the task of the pills. Sample BJ-Sample BL (TABLE 19) demonstrate that is possible to create complex flavors by mixing individual flavors. In this table, the pills have the distinct flavor of crème brûlée. The flavor combinations enhance the consumer experience with the pills by both masking any inherent flavors of the pill and/or provide a pleasant experience to the consumer.

Preparation of Composition

Compositions were prepared using a heated mixing device. An overhead mixer (IKA Works Inc, Wilmington, NC, model RW20 DMZ) and a three-blade impeller design was assembled. All preparations were heated on a heating-pad assembly (VWR, Radnor, PA, 7×7 CER Hotplate, cat. no. NO97042-690) where heating was controlled with an accompanying probe. All preparations were done in a 125 ml stainless steel beaker (Thermo Fischer Scientific, Waltham, MA).

Solutions were prepared by adding water (1), Sodium Myristate (2), sugar (10), and Vanilla (11) to the beaker. The beaker was placed on the heated mixing device. The overhead stirrer was placed in the beaker and set to rotate at 225 rpm. The heater was set, and the preparation was heated to 80° C. The solution was then poured in a sample cup and allowed to cool.

TABLE 18

|  | Sample BF Inventive | Sample BG Inventive | Sample BH Inventive | Sample BI Inventive |
|---|---|---|---|---|
| (1) Water | 24.046 g | 21.769 g | 24.259 g | 22.083 g |
| (2) NaC14 | 0.760 g | 0.755 g | — | — |
| (3) NaC16 | — | — | 0.5027 g | 0.5014 g |

TABLE 18-continued

|  | Sample BF Inventive | Sample BG Inventive | Sample BH Inventive | Sample BI Inventive |
| --- | --- | --- | --- | --- |
| (4) NaC18 | — | — | — | — |
| (10) Sugar | 0.257 g | 2.499 g | 0.2505 g | 2.5031 g |
| (11) Vanilla |  |  |  |  |
| Form | pass | pass | pass | pass |
| % Crystallizing Agent | 3.0% | 3.1% | 2.0% | 2.0% |
| % Flavors | 1.0% | 10.0% | 1.0% | 10.0% |

TABLE 19

|  | Sample BJ Inventive | Sample BK Inventive | Sample BL Inventive |
| --- | --- | --- | --- |
| (1) Water | 24.117 g | 24.038 g | 21.511 g |
| (2) NaC14 | 0.753 g | 0.778 g | 0.750 g |
| (3) NaC16 | — | — | — |
| (4) NaC18 | — | — | — |
| (10) Sugar | — | 0.0776 g | 2.517 g |
| (11) Vanilla | 0.266 g | 0.2525 g | 0.259 g |
| Form | pass | pass | pass |
| % Crystallizing Agent | 3.0% | 3.1% | 3.0% |
| % Flavors | 1.2% | 1.3% | 11.0% |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A rheological solid oral composition for delivering an oral active agent, comprising:
   a crystallizing agent comprising a blend of salts of fatty acids containing from 13 to 16 carbon atoms; wherein the crystallizing agent blend has an Optimal Purity (Po) of greater than about 0.3 and a Single Purity (Ps) of greater than about 0.5;
   an aqueous phase comprising water and a solvent; and
   an oral active agent;
   wherein the rheological solid composition comprises from about 80% to about 99.5% water and about 0.5% to about 15% solvent, by weight of the rheological solid oral composition;
   wherein the rheological solid oral composition has a crystalline mesh comprising a rigid,
   three-dimensional, interlocking crystalline skeleton framework of fiber-like crystalline particles formed from crystallizing agents, and the framework has voids or openings containing the aqueous phase and the oral active agent.

2. The rheological solid oral composition according to claim 1, having a firmness between 0.1 N and 50.0 N as determined by FIRMNESS TEST METHOD, and having a thermal stability of about 40° C. to about 95° C. as determined by THERMAL STABILITY TEST METHOD, and having a liquid expression of between about 100 J m-3 to about 6000 J m-3 as determined by AQUEOUS PHASE EXPRESSION TEST METHOD.

3. The rheological solid oral composition according to claim 1, wherein the crystallizing agent comprises a blend of salts of fatty acids containing 13 or 14 carbon atoms.

4. The rheological solid oral composition according to claim 1, wherein the crystallizing agent is a metal salt.

5. The rheological solid oral composition according to claim 4, wherein the metal salt is at least one of sodium palmitate or sodium myristate.

6. The rheological solid oral composition according to claim 1, wherein the crystallizing agent is present in an amount from about 0.01% to about 10%, by weight of the rheological solid oral composition.

7. The rheological solid oral composition according to claim 1, wherein the oral active agent is at least one of Antacids, H2 Antagonists, Proton Pump Inhibitors, Anesthetics, Antibiotics, Anticholinergics, Antihistamines, Antitussives, Antivirals, Decongestants, Demulcents, Expectorants, Mucolytics, Pain-Relieving Agents, Sleep Agents, or Dietary Supplements.

8. The rheological solid oral composition according to claim 7, wherein the Dietary Supplement is at least one Allergy Supplement Ingredients, Antioxidant Supplement Ingredients, Digestive Wellness/Gastrointestinal Ingredients, Enzymes, Immune Agents, Metabolics, Vitamins, Minerals, Neurologics, Pain Reducers, Sleep Agents, Stress Agents, Prebiotics, or Probiotics.

9. The rheological solid oral composition according to claim 7 wherein the Pain-Relieving Agent is acetaminophen.

10. The rheological solid oral composition according to claim 1 wherein the oral active agent is less than about 10% of the weight of the dosage form.

11. The rheological solid oral composition according to claim 1, having a static coefficient of friction of less than about 0.50.

12. A rheological solid oral composition for delivering an oral active agent, comprising:
    a crystallizing agent comprising a blend of salts of fatty acids containing from 13 to 16 carbon atoms; wherein the crystallizing agent blend has an Optimal Purity (Po) of greater than about 0.3 and a Single Purity (Ps) of greater than about 0.5;
    an aqueous phase comprising water and a solvent; and
    an oral active agent;
    wherein, the rheological solid oral composition has a firmness between about 0.1 N to about 50.0 N as determined by FIRMNESS TEST METHOD;

a thermal stability of about 40° C. to about 95° C. as determined by THERMAL STABILITY TEST METHOD;

a liquid expression of between about 100 J m-3 to about 8,000 J m-3 as determined by AQUEOUS PHASE EXPRESSION TEST METHOD;

wherein the oral active agent is at least one of Antacids, H2 Antagonists, Proton Pump Inhibitors, Anesthetics, Antibiotics, Anticholinergics, Antihistamines, Antitussives, Antivirals, Decongestants, Demulcents, Expectorants, Mucolytics, Pain-Relieving Agents, Sleep Agents, or Dietary Supplements; and wherein the rheological solid composition comprises from about 80% to about 99.5% water and about 0.5% to about 15% solvent, by weight of the rheological solid oral composition;

wherein the rheological solid oral composition has a crystalline mesh comprising a rigid, three-dimensional, interlocking crystalline skeleton framework of fiber-like crystalline particles formed from crystallizing agents, and the framework has voids or openings containing the aqueous phase and the oral active agent.

13. The rheological solid oral composition according to claim 12, wherein the Dietary Supplement is at least one Allergy Supplement Ingredients, Antioxidant Supplement Ingredients, Digestive Wellness/Gastrointestinal Ingredients, Enzymes, Immune Agents, Metabolics, Vitamins, Minerals, Neurologics, Pain Reducers, Sleep Agents, Stress Agents, Prebiotics, or Probiotics.

14. The rheological solid oral composition according to claim 11, wherein the crystallizing agent is a metal salt.

15. The rheological solid oral composition according to claim 12, having a static coefficient of friction of less than about 0.50.

* * * * *